United States Patent [19]

Hara et al.

[11] Patent Number: 5,401,775
[45] Date of Patent: Mar. 28, 1995

[54] TRI(LOWER ALKOXY)BENZENE DERIVATIVES

[75] Inventors: Hiromu Hara, Chiba; Tatsuya Maruyama, Ibaraki; Munetoshi Saito, Ibaraki; Toshiyasu Mase, Chiba, all of Japan

[73] Assignee: Yamanouchi Pharmaceutical Co., Ltd., Tokyo, Japan

[21] Appl. No.: 50,002
[22] PCT Filed: Oct. 18, 1991
[86] PCT No.: PCT/JP91/01429
  § 371 Date: Dec. 22, 1993
  § 102(e) Date: Dec. 22, 1993
[87] PCT Pub. No.: WO92/07819
  PCT Pub. Date: May 14, 1992

[30] Foreign Application Priority Data

Oct. 25, 1990 [JP] Japan ................... 2-287973

[51] Int. Cl.⁶ .................. A61K 31/17; C07C 275/34
[52] U.S. Cl. .................. 514/598; 514/238.2; 514/331; 514/438; 514/595; 514/596; 544/169; 546/235; 548/568; 564/47; 564/48; 564/52
[58] Field of Search .................. 564/52, 48, 47; 514/598, 596, 595

[56] References Cited

U.S. PATENT DOCUMENTS 3,049,562  8/1962  Wright et al. .................... 564/48
3,917,647 11/1975  Mihailovski .................... 564/52
4,252,804  2/1981  Joullié et al. .................... 564/52

FOREIGN PATENT DOCUMENTS 0259548  2/1990  Japan.

*Primary Examiner*—Shailendra Kumar

*Attorney, Agent, or Firm*—Burgess, Ryan and Wayne

[57] ABSTRACT

This invention relates to a tri(lower alkoxy)benzene derivative of the general formula (I), or its salt, optical isomer or solvate,

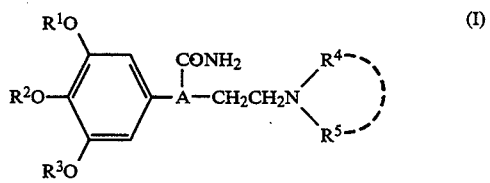

wherein:
  $R^1$, $R^2$ and $R^3$: same or different and each represents a lower alkyl group;
  A: a group of the formula $$-\overset{|}{C}H- \text{ or } -\overset{|}{N}-;$$

and
  $R^4$ and $R^5$: same or different and each represents a lower alkyl group, an aralkyl group or an aryl group, provided that $R^4$ and $R^5$ may, taken together with the adjacent nitrogen atom, form a pyrrolidinyl group, a piperidino group, a morpholino group, a thiomorpholino group, or a piperazinyl group optionally substituted by a lower alkyl group in 4-position;

to pharmaceutical compositions containing the same, and to processes for their production. The compound of the invention is useful as value as a pulmonary-surfactant secretion promoting agent.

9 Claims, 1 Drawing Sheet

TRI(LOWER ALKOXY)BENZENE DERIVATIVES

TECHNICAL FIELD

This invention relates to tri(lower alkoxy)-benzene derivatives and salts, optical isomers or solvates thereof, which are useful as medicaments, in particular, pulmonary surfactant secretion stimulants, to pharmaceutical compositions containing the same, and to processes for their production.

BACKGROUND ART

In animal lungs, there occurs a physiologically active substance, called pulmonary surfactant, which is mainly composed of phospholipids. The pulmonary surfactant is mostly biosynthesized in, and secreted from, type-II epithelial cells of the alveoli and exists not only in the alveolar region but also in the entire airway covering its internal wall. This substance is known to prevent collapse of the alveoli by reducing the surface tension and this is an important physiological function for the maintenance of respiratory function. Infant respiratory distress syndrome which may lead to acute respiratory failure occurs from a deficiency in pulmonary surfactant. Many reports indicate that such decrease or dysfunction of pulmonary surfactant is also found in adult respiratory distress syndrome. Hallman, et al. reported that an abnormality of pulmonary surfactant may occur also in chronic respiratory failure (Journal of Clinical Investigation, 70, 673–683, 1982).

Pulmonary surfactant plays an important role as a mechanism of defense in the whole respiratory tract, in addition to its anti-collapse action. Thus, its preventive effect against pulmonary edema, against the infection by bacteria and viruses, and against polluted atmosphere and antigens which might induce respiratory tract inflammation and asthmatic attacks has been described in many reports. In addition, pulmonary surfactant is known to be playing an important role in the removal of foreign matter from the airway by lubricating the respiratory tract lumen and activating mucociliary transport.

These multiple physiological functions which pulmonary surfactant is discharging in the respiratory system suggest that its qualitative change and quantitative reduction are associated with the onset and exacerbation of many respiratory diseases. Therefore, promoting the secretion of pulmonary surfactant will probably make it possible to treat or prevent various respiratory diseases, such as acute respiratory failure (e.g., infant or adult respiratory distress syndrome), acute and chronic bronchitis, infectious diseases, asthma and chronic respiratory failure.

It is also likely that administration of pulmonary surfactant to a pregnant woman who has a potential to be delivered of a premature child will prevent the incidence of infant respiratory distress syndrome.

Heretofore, attempts have been made to utilize the natural or a recombinant pulmonary surfactant as it is or a composition containing the same (JP-B-1-13690, the term "JP-B" as used herein means an "examined Japanese patent publication", JP-A(PCT)-63-501792 and JP-A-2-53798, the term "JP-A" as used herein means an "unexamined published Japanese patent application"). However, only ambroxol, which is commercially available as an expectorant (Merck Index 11, pp. 62–63, 392, Ambroxol), may be reckoned as the substance that has ever been found to have the activity to promote the secretion of pulmonary surfactant (Post. et al.: Lung, 161, 349–359, 1983).

Meanwhile, among tri(lower alkoxy)benzene derivatives, a trimethoxybenzene substituted by a group of the formula

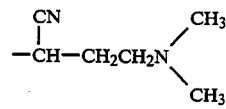

is disclosed in Journal of Medicinal Chemistry, 9, 631, 1966 as a compound having antihistaminic activity. JP-A-62-240653 discloses a compound of the following formula as an antianginal agent.

wherein $R_1$ and $R_4$ independently represent a phenyl group which may optionally be substituted by 1, 2 or 3 members of halogen, trifluoromethyl, $C_{1-4}$ alkoxy, $C_{1-4}$ alkyl, cyano, hydroxy, nitro, $NR_5R_6$ and $O_2SNR_5$—$R_6$ (where $R_5$ and $R_6$ independently represent hydrogen or $C_{1-6}$ alkyl, or jointly represent $C_{3-6}$ polymethylene) or a phenyl group which may be di-substituted by $C_{1-2}$ alkylenedioxy in the adjacent carbon positions and optionally by one member of said groups; $R_2$ is selected from among $(CH_2)_zCN$ (where z is 0 or an integer of 1 through 4), $C_{1-12}$ alkyl, $C_{3-7}$ cycloalkyl, $C_{3-7}$ cycloalkyl-$C_{1-4}$ alkyl, phenyl-$C_{1-4}$ alkyl, pyridyl, pyridyl-$C_{1-4}$ alkyl, $COR_7$, $COCH_2COR_7$, $SO_2R_7$, $CO_2R_7$, $CONHR_7$ and $CSNHR_7$ (where $R_7$ is selected from among $C_{3-12}$ alkyl, $C_{3-7}$ cycloalkyl, $C_{3-7}$ cycloalkyl-$C_{1-4}$ alkyl, phenyl and phenyl-$C_{1-4}$ alkyl and the optional alkyl moiety of $R_7$ may optionally be substituted by hydroxy or $C_{1-4}$ alkanoyloxy), the optional pyridyl or phenyl moiety of $R_2$ may optionally be substituted as defined for $R_1$ and $R_4$ and the optional cycloalkyl moiety of $R_2$ may optionally be substituted by 1 or 2 $C_{1-4}$ alkyls; $R_3$ represents hydrogen or $C_{1-4}$ alkyl; A represents $C_{2-6}$ alkylene; and B represents $C_{1-4}$ alkylene.

However, the above literature neither disclose nor suggest that any tri(lower alkoxy)benzene derivative ever promotes secretion of pulmonary surfactant.

DISCLOSURE OF INVENTION

Under the circumstances, the inventors of the present invention have proceeded with a screening of many synthetic compounds for the purpose of developing a compound having improved pulmonary surfactant secretion promoting activity, and as a result, found that a novel tri(lower alkoxy)benzene derivative of the following general formula (I) and its salts, optical isomers and the like have pulmonary surfactant secretion promoting activity surpassing that of ambroxol. The present invention has been completed on the basis of these findings.

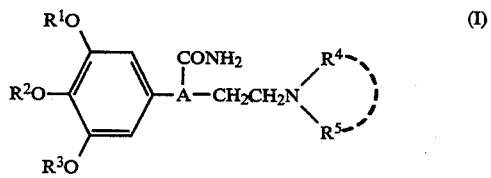

wherein $R^1$, $R^2$ and $R^3$, which are the same or different, each represents a lower alkyl group; A represents a group of the formula

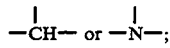

and $R^4$ and $R^5$, which are the same or different, each represents a lower alkyl group, an aralkyl group or an aryl group, provided that $R^4$ and $R^5$ may, taken together with the adjacent nitrogen atom, form a pyrrolidinyl group, a piperidino group, a morpholino group, a thiomorpholino group, or a piperazinyl group optionally substituted by a lower alkyl group in 4-position)

The compound (I) of the present invention is structurally characterized by being a tri(lower alkoxy)-benzene substituted by a group of the formula

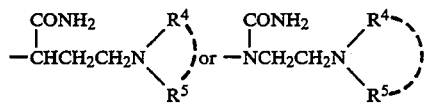

(wherein $R^4$ and $R^5$ have the same meanings as defined hereinbefore).

The compound described in the above-mentioned Journal of Medicinal Chemistry differs from the compound (I) of the present invention in that the former has a group of the formula:

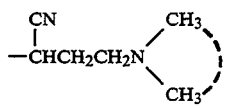

as the substituent.

On the other hand, the compound described in the above-mentioned JP-A-62-240653 is limited to $C_{3-12}$ alkyl for $R_7$ in the optional $CONHR_7$ group for $R_2$ and does not encompass hydrogen for $R_7$. Furthermore, the compound represented by a general formula therein literally includes compounds in which $R_1$ represents trialkoxyphenyl but there are no relevant specific examples and, in the examples given, only 3,4-dimethoxyphenyl, phenyl and 4-chlorophenyl are mentioned.

Therefore, the compound (I) of the present invention is a novel compound which is structurally distinguished from those known compounds.

The compound of the invention is now described in detail.

The term "lower" used in the definitions of the general formulas presented in this specification means, unless otherwise indicated, a linear or branched carbon chain containing 1 to 6 carbon atoms.

Therefore, the "lower alkyl group" mentioned hereinbefore specifically includes methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and so on.

The "aryl group" preferably includes phenyl and naphthyl.

In addition, the "aralkyl group" is preferably a group corresponding to the above "lower alkyl group" in which the optional hydrogen atom is substituted with the above "aryl group". Thus, taking phenyl as an example of the aryl group, there can be mentioned benzyl, phenethyl, 3-phenylpropyl, 2-phenylpropyl, 1-phenylpropyl, 4-phenylbutyl, 3-phenylbutyl, 2-methyl-3-phenylpropyl, 5-phenylpentyl, 6-phenylpentyl, benzhydril, trityl and so on.

In the preferred specific compounds of the present invention, $R^4$ and $R^5$ are lower alkyl, particularly methyl.

The compound (I) of the invention may be in the form of a salt. The present invention encompasses such salts within its purview. The satls of the compound (I) include acid addition salts with inorganic acids such as hydrochloric acid, hydrobromic acid, hydroiodic acid, sulfuric acid, nitric acid, phosphoric acid, etc., or organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, etc.; salts with acidic amino acids such as glutamic acid, aspartic acid, etc.; and ammonium salts thereof.

Where the substituent A in the compound (I) of the present invention is

the carbon atom in the radical is an asymmetric carbon and hence gives rise to optical isomers. The present invention also encompasses each of such optical isomers as discrete entities and mixtures of the isomers.

Furthermore, the present invention encompasses various solyates and polymorphs of compound (I).

The compound (I) of the present invention can be produced by a variety of synthetic processes, utilizing the characteristics of its skeletal structure and substituent groups. Typical examples of the production processes are described below.

Process 1

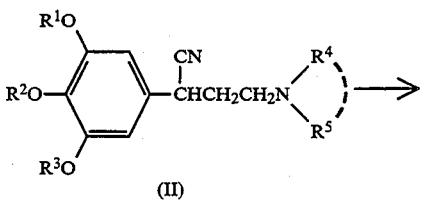

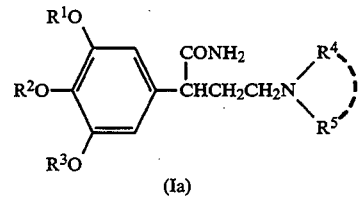

Process 2

-continued

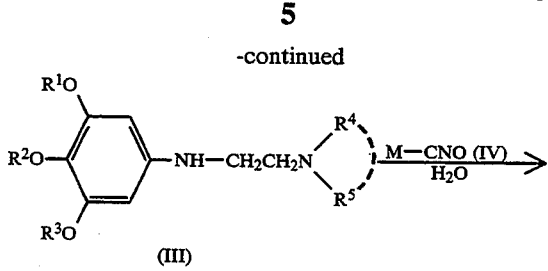

(III)

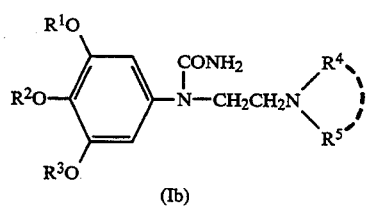

(Ib)

(In the above reaction formulas, $R^1$, $R^2$, $R^3$, $R^4$ and $R^5$ are as defined hereinbefore; M represents a hydrogen atom or an alkali metal).

Examples of the alkali metal which can be used here includes potassium and sodium.

The respective processes are now described in detail.

PROCESS 1

The butyramide derivative of general formula (Ia) in which A is

can be produced by hydrolyzing the corresponding butyronitrile derivative of general formula (II).

Since there is no risk of overhydrolysis in this reaction, alkali hydrolysis using an alcoholic caustic alkali solution can be employed.

This reaction can be carried out with advantage in the presence of a caustic alkali, e.g. sodium hydroxide or potassium hydroxide, in an alcohol such as tert-butanol at an elevated temperature not lower than 50° C.

The starting compound (II) can be easily provided by the process described, for example, in the above-mentioned Journal of Medicinal Chemistry or any process analogous thereto (cf. the reaction formulas presented below).

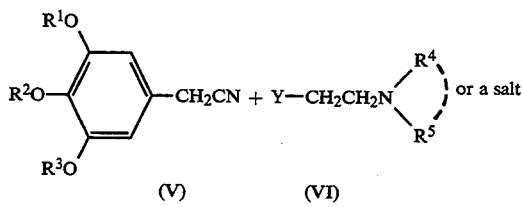

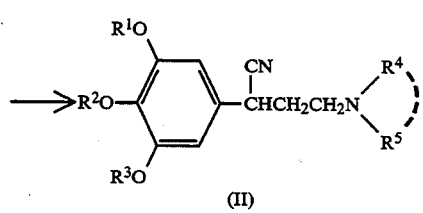

(In the above reaction formulas, $R^1$, $R^2$, $R^3$, $R^4$ and $R^5$ are as defined hereinbefore, Y represents a halogen atom.)

Thus, the starting compound (II) can be easily provided by reacting a tri(lower alkoxy)phenylacetonitrile of general formula (V) with a substituted aminoethyl halide of general formula (VI) or a salt thereof.

This reaction is carried out using compound (V) and at least equimolar amount of compound (VI) or a salt thereof in the presence of a base, e.g. sodium hydride, sodium hydroxide, potassium hydroxide, or an alkali metal alkoxide such as sodium ethoxide (about 2 equivalents when a salt of (VI) is used, and other about 1 equivalent otherwise) in an inert organic solvent, e.g., N,N-dimethylformamide, dimethyl sulfoxide, etc., usually at room temperature or, if required, at an elevated temperature.

PROCESS 2

The urea compound of general formula (Ib), which is among the objective compounds of the present invention, can be synthesized by reacting an ethylenediamine compound of general formula (III) with an isocyanic acid or an alkali metal isocyanate.

This reaction can be conducted with advantage using approximately equivalent amount of compound (III) and compound (IV) either in the absence of a solvent or in an inert solvent such as water, an organic solvent, e.g., acetic acid, benzene, toluene, xylene, chlorobenzene, chloroform, dichloromethane, acetone, tetrahydrofuran, etc., or a mixture of such solvents, generally at room temperature or, if required, under heating for a short time.

The starting compound (III) for this reaction can be easily provided by the reaction of a 3,4,5-tri(lower alkoxy)aniline with an N,N-disubstituted aminoethyl halide.

The reaction product obtained in each of the above processes can be isolated and purified in the free form or in the form of a suitable salt or solvate. The salt can be prepared by ordinary salt-forming reactions.

The isolation and purification can be effected by the ordinary chemical procedures such as extraction, concentration, distillation, crystallization, filtration, recrystallization and various kinds of chromatography.

The optical isomers of the present invention can be obtained by an optical resolution technique. This technique utilizes a difference in physical constant between the diastereomers which form on reaction of a racemic compound to be resolved and a chiral compound. Since the objective compound of the present invention is an amine, the desired isomer can be obtained by preparing a crystallizable diastereomer salt using an optically active acid as the chiral compound, subjecting the salt to fractional crystallization to separate the insoluble salt, and subjecting this salt to double decomposition.

The optically active acid which can be used for this purpose includes:

(+) or (−)-cis-2-Benzamidocyclohexanecarboxylic acid;
(+) or (−)-trans-2-Benzamidocyclohexanecarboxylic acid;
(+) or (−)-Di-p-toluoyl-L- or D-tartaric acid;
(+) or (−)-Dibenzoyl-L- or D-tartaric acid;
(+) or (−)-Diacetyl-L- or D-tartaric acid;
(−)-Malic acid;
(−)-Camphanic acid;
(+)-Camphor-10-sulfonic acid; and (+)-Mandelic acid There can also be used acidic amino acids such as aspartic acid, glutamic acid and so on.

Aside from the above diastereomer salt method of resolution, the desired optical isomer can be separated by optically active chromatograpny as well.

INDUSTRIAL APPLICABILITY

Figure 1:
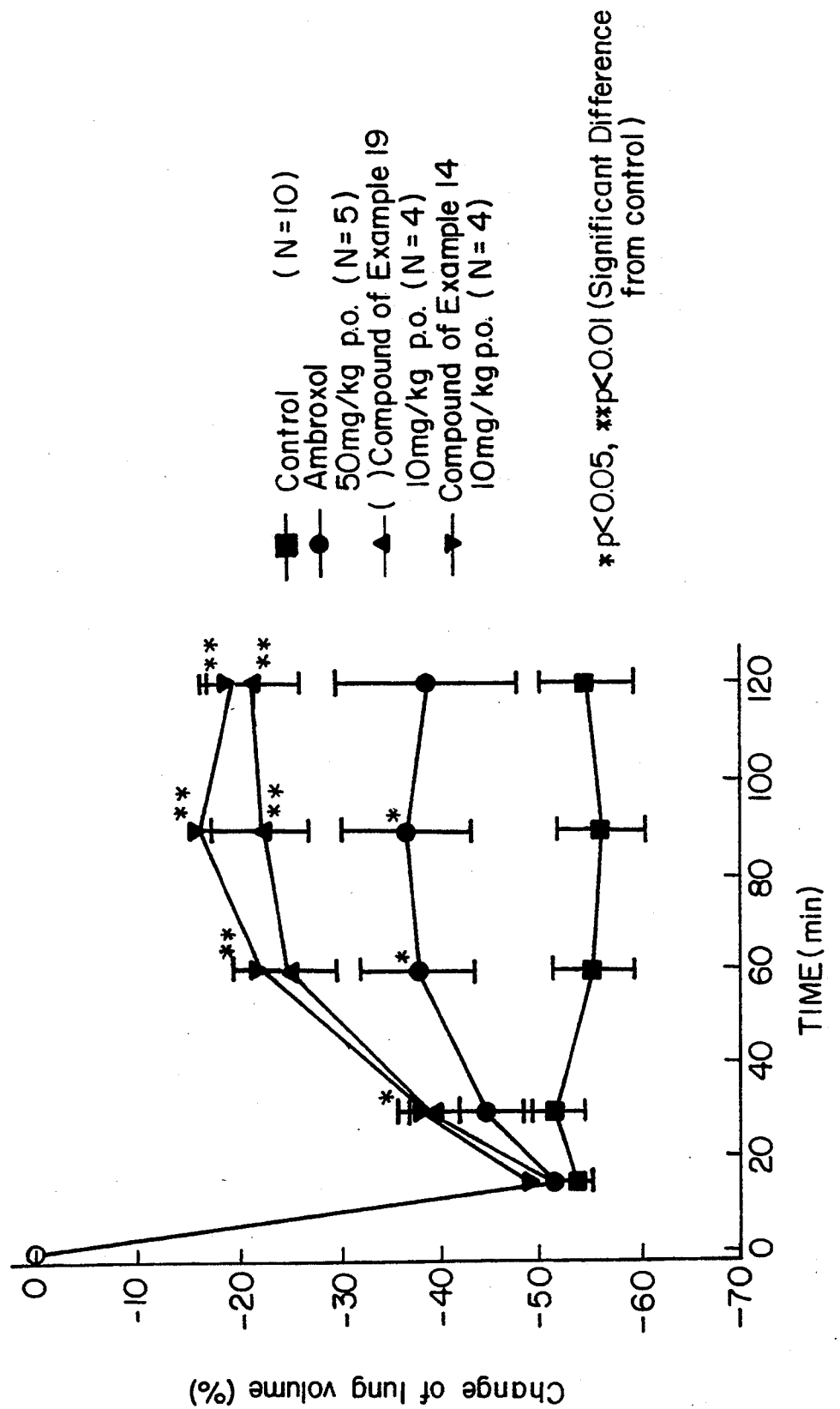
FIG. 1 shows the results of an experimental study using pulmonary compliance as an indicator of respiratory function recovery after pulmonary lavage with a surface active agent in Test Example 2. The vertical axis represents the percentage change (% change) of lung volume as compared with the baseline data prior to lavage with Tween 20 (trade name of Kao-Atlas, polyoxyethylene sorbitan fatty acid ester; hereinafter, referred to briefly as "Tween 20") and the horizontal axis presents the time (min.). — — represents control (N=10); — — ambroxol, 50 mg/kg p.o. (N=5); — — the optically active (+) compound of Example 19, 10 mg/kg p.o. (N=4); and —▽— the compound of Example 14, 10 mg/kg p.o. (N=4). N means the number of guinea pigs used; "*" means a significant difference from control at the level of p<0.05; and "**" means a significant difference from control at the level of p<0.01.

The compound (I) and its salts, optical isomers and solvates of the present invention have the action of promoting the secretion of pulmonary surfactant, and are therefore useful for the treatment and prevention of diseases manifesting decrease, deficiencies, or dysfunction of this substance, such as infant respiratory distress syndrome, adult respiratory distress syndrome, pulmonary edema, acute or chronic respiratory failure, acute or chronic bronchitis, various infections, asthma and other respiratory organ diseases.

TEST EXAMPLE 1

Pulmonary Surfactant Secretion Stimulating Activity

Experimental Method:

Male Hartley guinea pigs weighing 300 to 350 g were used in the experiment.

The compound was administered intraperitoneally to guinea pigs in a single dose of 50 mg/kg and after an interval of 3 hours, the animals were sacrificed by exsanguination from the abdominal aorta and vena cava under anesthesia with 100 mg/kg of pentobarbital sodium. Using 10 ml/kg of ice-cooled physiological saline, bronchoalveolar lavage was carried out twice. The combined bronchoalveolar lavage fluid was centrifuged at 1000 rpm for 10 minutes at 4° C. and the supernatant was subjected to the assay of pulmonary surfactant as shown below.

Lipids were extracted from each lavage supernatant by the method of Folch et al. (Journal of Biological Chemistry 226, 497–502, 1957), and its main component, saturated phosphatidylcholine, was then extracted as an indicator of pulmonary surfactant by the method of Gilfillan et al. (Journal of Lipid Research, 24, 1651–1656, 1983). Thus, the lipid was extracted with chloroform-methanol (2:1) and the unsaturated lipid was oxidized with osmic acid (100 mg/ml). Then, the saturated phosphatidylcholine was extracted with chloroform-methanol-7N aqueous ammonia (70:30:2) by using a neutral alumina column. The saturated phosphatidylcholine was assayed with Nescoat PL Kit-K (Nippon Shoji Co., Ltd.), and the percent increase compared to the control group (solvent) was determined.

Results:

The study of the pulmonary surfactant secretion stimulating effect of the compound of this invention by the above method showed that both the compounds of Example 7 and Example 14, for example, exhibits the action of promoting the secretion of pulmonary surfactant by not less than 30% relative to the control.

TEST EXAMPLE 2

Respiratory Function Recovery After Tween 20 Pulmonary Lavage

Experimental Method:

Bronchoalveolar lavage with the surface active agent Tween 20 results in removal of pulmonary surfactant and, hence, in respiratory dysfunction. The effect of compounds on respiratory function recovery was studied by comparing the static.compliances before and after Tween 20 bronchoalveolar lavage.

Male Hartley guinea pigs (body weights: 650–750 g) were treated with gallamine (1 mg/kg, i.p.) to arrest spontaneous respiration under urethane anesthesia (1.2 g/kg, i.p.), and the animals were put under artificial ventilation at 10 ml/kg and 60 ventilations/min. Then, bronchoalveolar lavage was performed twice using 3.8% aqueous solution of Tween 20 (10 ml/kg). The test compound was administered orally 5 minutes after Tween 20 lavage. The interval volume of the lungs was serially measured at a pressure of 15 $cmH_2O$ as static compliance.

Results:

The results of the above experiment are shown in FIG. 1.

It will be apparent from FIG. 1 that the compounds of Examples 14 and 19 significantly stimulated the recovery of static compliance even at one-fifth of the dose of ambroxol (control compound), indicating that their activity is remarkably higher than that of ambroxol.

The pharmaceutical composition containing one or more of the compound of the present invention can be manufactured by formulating the active compound with the common pharmaceutical carriers, excipients and other additives and be provided in a variety of dosage forms such as tablets, powders, fine granules, granules, capsules, pills, oral liquids (inclusive of syrups), injections, inhalants, suppositories, transdermal therapeutic liquids, ointments, percutaneous therapeutic patches, transmucosal therapeutic patches (e.g. buccal patch) or liquids (e.g. transnasal therapeutic sprays), and so on. These preparations are administered orally, parenterally or via maternal bodies.

The clinical dosage of the compound of the present invention is properly selected according to the diagnosis, symptoms, body weight, age and sex of each patient, the route of administration, and other factors.

For example, for use in infant respiratory distress syndrome, the daily dosage is 1 to 500 mg for intravenous injection, and 1 to 5000 mg, preferably 1 to 2000 mg, for administration via the maternal body. In other diseases, the oral dosage for a human adult is 1 to 2000 mg, preferably 1 to 500 mg, and the parenteral dosage for an adult is 1 to 2000 mg, preferably 1 to 500 mg. The above dosage can be administered in a single dose or in 2 to 4 divided doses.

The following examples will further illustrate the invention.

BEST MODE FOR CARRYING OUT THE INVENTION

EXAMPLE 1

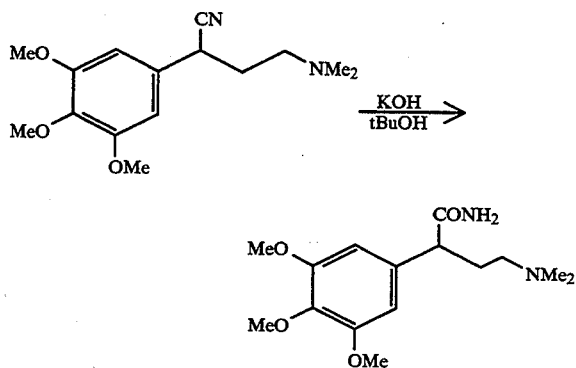

In 8 ml of 2-methyl-2-propanol was dissolved 0.84 g of 4-dimethylamino-2-(3,4,5-trimethoxyphenyl)-butyronitrile, followed by addition of 1.0 g of ground potassium hydroxide. The mixture was refluxed for 1 hour. After cooling the reaction mixture, the insoluble matters were filtered off and the filtrate was concentrated under reduced pressure. To the residue thus obtained were added ethyl acetate and 10% hydrochloric acid. The aqueous layer was separated and made strongly basic with sodium hydroxide for salting-out and the basic substance was extracted with ethyl acetate. The ethyl acetate layer was washed with a mixture of water and saturated aqueous sodium chloride (1:1) and a saturated aqueous solution of sodium chloride in turn, then dried over anhydrous sodium sulfate and concentrated to dryness under reduced pressure. The crystalline residue thus obtained (0.59 g) was recrystallized from ethyl acetate to provide 0.35 g of 4-dimethylamino-2-(3,4,5-trimethoxyphenyl)butyramide.

Physicochemical properties:
Melting point: 110°–112° C.

| Elemental analysis for $C_{15}H_{24}N_2O_4$ | | | |
|---|---|---|---|
| | C (%) | H (%) | N (%) |
| Calcd. | 60.79 | 8.16 | 9.45 |
| Found | 60.56 | 8.11 | 9.39 |

The following compounds of Examples 2 through 6 were prepared in the same manner as Example 1.

EXAMPLE 2

4-Diethylamino-2-(3,4,5-trimethoxyphenyl)butyramide

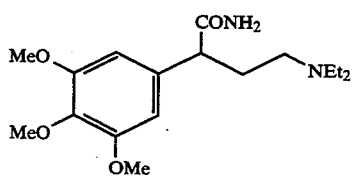

Starting compound: 4-Diethylamino-2-(3,4,5-trimethoxyphenyl)butyronitrile
Physicochemical properties:
Mass spectrum (m/z): 324 (M+)
NMR spectrum (CDCl$_3$, TMS internal standard)
δ: 0.97 (6H, t, J=7Hz), 1.7–2.4 (4H, m), 2.50 (4H, q, J=7Hz), 3.48 (1H, t, J=8Hz), 3.81 (3H, s), 3.83 (6H, s), 5.30 (1H, br s), 5.80 (1H, br s), 6.49 (2H, s)

EXAMPLE 3

4-(1-Pyrrolidinyl)-2-(3,4,5-trimethoxyphenyl)butyramide

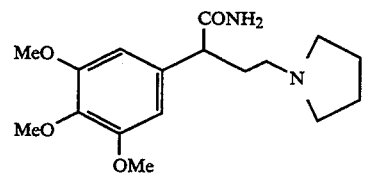

Starting compound: 4-(1-Pyrrolidinyl)-2-(3,4,5-trimethoxyphenyl)butyronitrile
Physicochemical properties:
Mass spectrum (m/z): 322 (M+)
NMR spectrum (CDCl$_3$, TMS internal standard)
δ: 1.7–2.0 (4H, m), 1.9–2.4 (2H, m), 2.4–2.7 (6H, m), 3.54 (1H, t, J=7Hz), 3.83 (3H, s), 3.86 (6H, s), 5.40 (1H, br s), 5.87 (1H, br s), 6.54 (2H, s)

EXAMPLE 4

4-Piperidino-2-(3,4,5-trimethoxyphenyl)butyramide

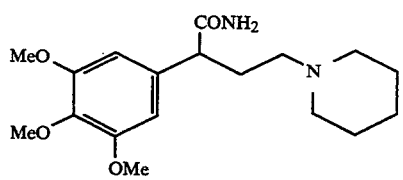

Starting compound: 4-Piperidino-2-(3,4,5-trimethoxyphenyl)butyronitrile
Physicochemical properties:

| Elemental analysis for $C_{18}H_{28}N_2O_4 \cdot 0.3$ EtOAc | | | |
|---|---|---|---|
| | C (%) | H (%) | N (%) |
| Calcd. | 63.55 | 8.44 | 7.72 |
| Found | 63.38 | 8.45 | 7.95 |

Mass spectrum (m/z): 336 (M+)

EXAMPLE 5

4-Morpholino-2-(3,4,5-trimethoxyphenyl)butyramide

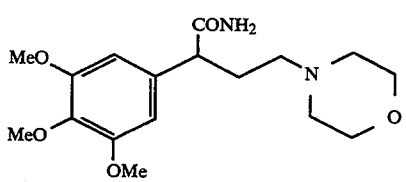

Starting compound: 4-Morpholino-2-(3,4,5-trimethoxyphenyl)butyronitrile
Physicochemical properties:
Mass spectrum (m/z): 338 (M+)
NMR spectrum (CDCl$_3$, TMS internal standard)
δ: 1.7–2.2 (2H, m), 2.2–2.5 (6H, m), 3.48 (1H, t, J=7Hz), 3.6–3.8 (4H, m), 3.80 (3H, s), 3.82 (6H, s), 5.52 (2H, br s), 6.48 (2H, s)

EXAMPLE 6

4-(N-Ethyl-N-phenylamino)-2-(3,4,5-trimethoxyphenyl)butyramide

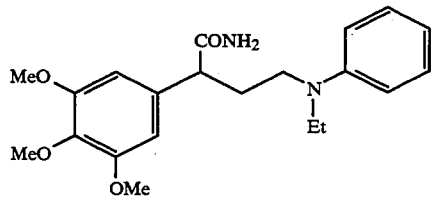

Starting compound: 4-(N-Ethyl-N-phenylamino)-2-(3,4,5-trimethoxyphenyl)butyronitrile
Physicochemical properties:
Melting point: 162°–164° C.

| Elemental analysis for $C_{21}H_{28}N_2O_4$ | | | |
|---|---|---|---|
| | C (%) | H (%) | N (5) |
| Calcd. | 67.72 | 7.58 | 7.52 |
| Found | 67.89 | 7.62 | 7.49 |

EXAMPLE 7

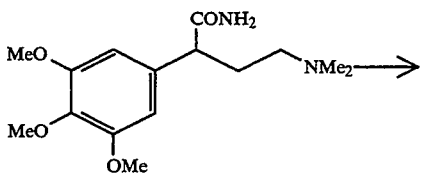

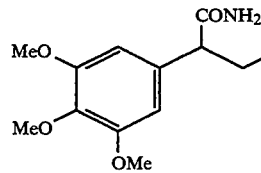

In 30 ml of ethanol was dissolved 10.8 g of 4-dimethylamino-2-(3,4,5-trimethoxyphenyl)butyramide, followed by addition of a mixture of concentrated hydrochloric acid (3 ml) and ethanol (27 ml). The mixture was stirred at a room temperature for 2 hours. The resulting precipitate was recovered by filtration and dried under reduced pressure to provide 12.2 g of 4-dimethylamino-2-(3,4,5-trimethoxyphenyl)butyramide hydrochloride.
Physicochemical properties:
Melting point: 194°–197° C.

| Elemental analysis for $C_{15}H_{25}N_2O_4Cl.0.6\ H_2O$ | | | |
|---|---|---|---|
| | C (%) | H (%) | N (%) | Cl (%) |
| Calcd. | 52.43 | 7.68 | 8.15 | 10.32 |
| Found | 52.52 | 7.81 | 8.15 | 10.59 |

The above compound formed a stable dihydrate after 6 days of standing in an atmosphere of 74% RH.
The following compounds of Example 8 to Example 12 were prepared in the same manner as Example 7.

EXAMPLE 8

4-Diethylamino-2-(3,4,5-trimethoxyphenyl)-butyramide hydrochloride

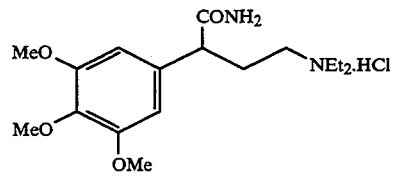

Starting compound: 4-Diethylamino-2-(3,4,5-trimethoxyphenyl)butyramide
Physicochemical properties:
Melting point: 60°–64° C.

| Elemental analysis for $C_{17}H_{29}N_2O_4Cl.1.3\ H_2O$ | | | |
|---|---|---|---|
| | C (%) | H (%) | N (%) | Cl (%) |
| Calcd. | 53.13 | 8.29 | 7.29 | 9.23 |
| Found | 53.29 | 8.42 | 6.83 | 9.17 |

EXAMPLE 9

4-(1-Pyrrolidinyl)-2-(3,4,5-trimethoxyphenyl)-butyramide hydrochloride

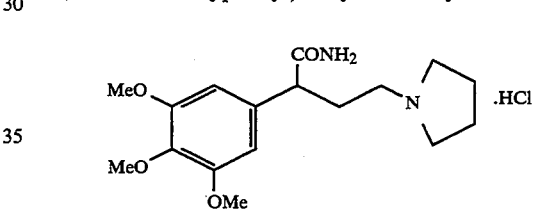

Starting compound: 4-(1-Pyrrolidinyl)-2-(3,4,5-trimethoxyphenyl)butyramide
Physicochemical properties:
Melting point: 201°–203° C.

| Elemental analysis for $C_{17}H_{27}N_2O_4Cl$ | | | |
|---|---|---|---|
| | C (%) | H (%) | N (%) | Cl (%) |
| Calcd. | 56.90 | 7.58 | 7.81 | 9.88 |
| Found | 56.66 | 7.62 | 7.67 | 10.09 |

EXAMPLE 10

4-Piperidino-2-(3,4,5-trimethoxyphenyl)butyramide hydrochloride

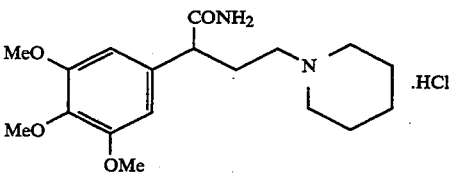

Starting compound: 4-Piperidino-2-(3,4,5-trimethoxyphenyl)butyramide
Physicochemical properties:
Melting point: 192°–195° C.

| Elemental analysis for C₁₈H₂₉N₂O₄Cl·0.8 H₂O | | | | |
|---|---|---|---|---|
| | C (%) | H (%) | N (%) | Cl (%) |
| Calcd. | 55.82 | 7.96 | 7.23 | 9.15 |
| Found | 56.02 | 7.86 | 6.93 | 9.28 |

EXAMPLE 11

4-Morpholino-2-(3,4,5-trimethoxyphenyl)butyramide hydrochloride

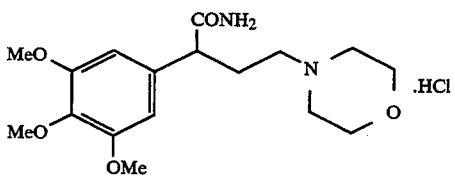

Starting compound: 4-Morpholino-2-(3,4,5-trimethoxyphenyl)butyramide
Physicochemical properties:
Melting point: 222°–224° C.
NMR spectrum (DMSO-d₆, TMS internal standard)
δ: 2.0–2.5 (2H, m), 2.7–3.3 (4H, m), 3.2–3.6 (3H, m), 3.61 (3H, s), 3.74 (6H, s), 3.6–4.0 (4H, m), 6.64 (2H, s), 6.92 (1H, br s), 7.54 (1H, br s), 11.55 (1H, br s)

EXAMPLE 12

4-(N-Ethyl-N-phenylamino)-2-(3,4,5-trimethoxyphenyl)butyramide hydrochloride

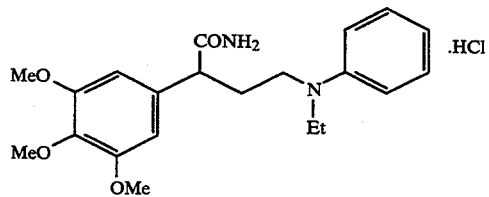

Starting compound: 4-(N-Ethyl-N-phenylamino)-2-(3,4,5-trimethoxyphenyl)butyramide
Physicochemical properties:
Melting point: 105°–110° C.

| Elemental analysis for C₂₁H₂₉N₂O₄Cl·0.6 H₂O | | | | |
|---|---|---|---|---|
| | C (%) | H (%) | N (%) | Cl (%) |
| Calcd. | 60.09 | 7.25 | 6.67 | 8.45 |
| Found | 60.04 | 7.41 | 6.57 | 8.72 |

EXAMPLE 13

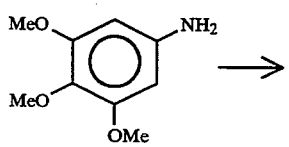

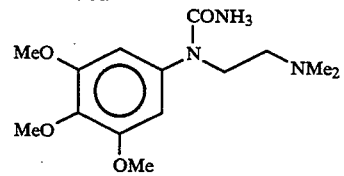

To a solution of 1.59 g of 3,4,5-trimethoxyaniline in 15 ml of dichloromethane was added 10 ml of trifluoroacetic anhydride. The mixture was stirred at a room temperature for 1 hour, and then the solvent was distilled off under reduced pressure. To a solution of the residue in 30 ml of acetone were added 1.32 g of 2-chloroethyldimethylamine hydrochloride and 7.3 g of ground potassium hydroxide. The reaction mixture was refluxed for 2 hours, and then 30 ml of water was added thereto, followed by stirring at a room temperature for 5 hours. This reaction mixture was concentrated under reduced pressure and the concentrate was diluted and acidified with 1N-hydrochloric acid. This aqueous solution was washed with ethyl acetate, made basic with sodium hydroxide and the product was extracted with ethyl acetate. The organic layer was washed with saturated aqueous solution of sodium chloride and dried over anhydrous sodium sulfate. The solvent was then distilled off under reduced pressure and the residue was purified by silica gel chromatography (eluent: chloroformmethanol=10:1) to provide 0.32 g of an oily product.

To a solution of 0.32 g of the oily product in a mixture of 5 ml of acetic acid and 5 ml of water was added a solution of 0.23 g of potassium isocyanate in 3 ml of water dropwise. This reaction mixture was stirred at a room temperature for 3.5 hours, diluted with water and made basic with sodium hydroxide. The product was extracted with ethyl acetate. The organic layer was washed with saturated aqueous solution of sodium chloride and dried over anhydrous sodium sulfate. The solvent was distilled off under reduced pressure and the residue was recrystallized from ethyl acetate-hexane to provide 0.24 g of 1-(2-dimethylaminoethyl)-1-(3,4,5-trimethoxyphenyl)urea.

Physicochemical properties:
Mass spectrum (m/z): 298 (MH+)
NMR spectrum (CDCl₃, TMS internal standard)
δ: 2.26 (6H, s), 2.43 (2H, t, J=7Hz), 3.75 (2H, t, J=7Hz), 3.85 (6H, s), 3.86 (3H, s 4.53 (2H, br s), 6.57 (2H, s)

EXAMPLE 14

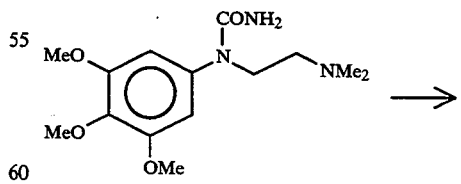

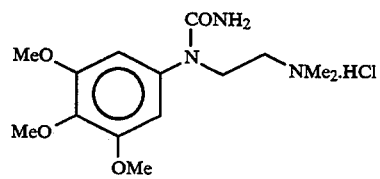

To a solution of 220 mg of 1-(2-dimethylaminoethyl)-1-(3,4,5-trimethoxyphenyl)urea in a mixture of ethanol (3 ml) and diethyl ether (15 ml) was added 4N-HCl-dioxane dropwise with stirring. The resulting crystals were collected by filtration and dried under reduced pressure to provide 230 mg of 1-(2-dimethylaminoethyl)-1-(3,4,5-trimethoxyphenyl)urea hydrochloride.

Physicochemical properties:
Melting point: 184°–186° C.

Elemental analysis for $C_{14}H_{24}N_3O_4Cl \cdot H_2O$

|  | C (%) | H (%) | N (%) | Cl (%) |
|---|---|---|---|---|
| Calcd. | 47.79 | 7.45 | 11.94 | 10.08 |
| Found | 47.54 | 7.24 | 11.91 | 10.26 |

EXAMPLE 15

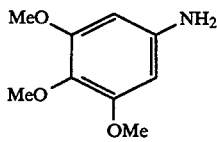

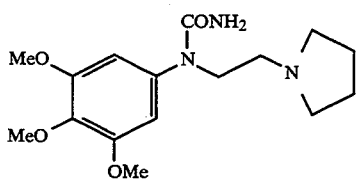

1-[2-(1-Pyrrolidinyl)ethyl]-1-(3,4,5-trimethoxyphenyl)urea was prepared in the same manner as Example 13.

Starting compound: 3,4,5-Trimethoxyaniline and 1-(2-chloroethyl)pyrrolidine hydrochloride Physicochemical properties:
Melting point: 130°–131.5° C.

Elemental analysis for $C_{16}H_{25}N_3O_4$

|  | C (%) | H (%) | N (%) |
|---|---|---|---|
| Calcd. | 59.43 | 7.79 | 12.99 |
| Found | 59.29 | 7.76 | 12.83 |

EXAMPLE 16

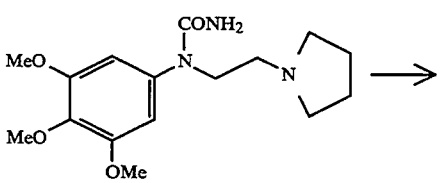

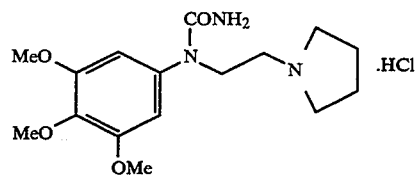

1-[2-(1-Pyrrolidinyl)ethyl]-1-(3,4,5-trimethoxyphenyl)urea hydrochloride was prepared in the same manner as Example 14.

Starting compound: 1-[2-(1-Pyrrolidinyl)ethyl]-1-(3,4,5-trimethoxyphenyl)urea

Physicochemical properties:
Melting point: 173°–175.5° C.

Elemental analysis for $C_{16}H_{25}N_3O_4 \cdot 1.3(H_3ClO)$

|  | C (%) | H (%) | N (%) | Cl (%) |
|---|---|---|---|---|
| Calcd. | 48.75 | 7.39 | 10.66 | 11.69 |
| Found | 48.70 | 7.25 | 10.73 | 11.75 |

EXAMPLE 17

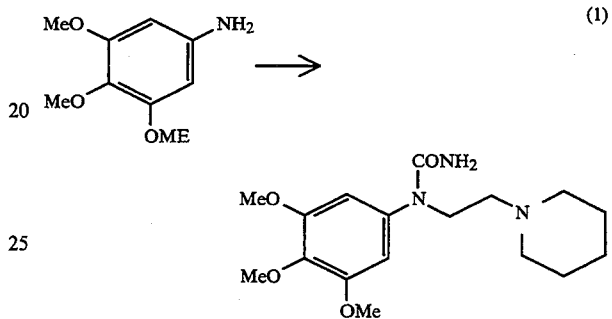

1-(2-(Piperidinoethyl)-1-(3,4,5-trimethoxyphenyl)urea was prepared in the same manner as Example 13.

Starting compound: 3,4,5-Trimethoxyaniline and 1-(2-chloroethyl)piperidine hydrochloride Physicochemical properties:

Elemental analysis for $C_{17}H_{27}N_3O_4$

|  | C (%) | H (%) | N (%) |
|---|---|---|---|
| Calcd. | 60.51 | 8.07 | 12.45 |
| Found | 60.27 | 8.10 | 12.35 |

EXAMPLE 18

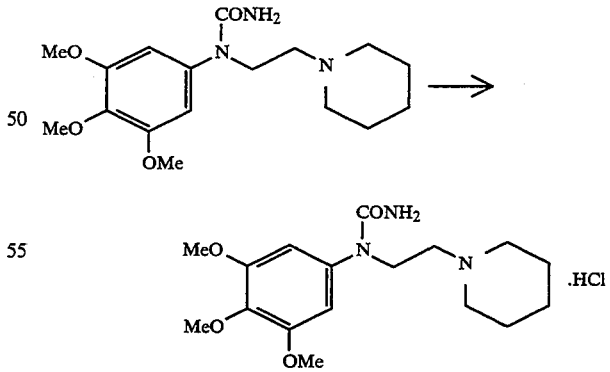

1-(2-Piperidinoethyl)-1-(3,4,5-trimethoxyphenyl)urea hydrochloride was obtained in the same manner as Example 14.

Starting compound: 1-(2-Piperidinoethyl)-1-(3,4,5-trimethoxyphenyl)urea

Physicochemical properties:
Melting point: 168°–172° C.

Elemental analysis for $C_{17}H_{27}N_3O_4 \cdot 2HCl \cdot 0.5\ H_2O$

|  | C (%) | H (%) | N (%) |
|---|---|---|---|
| Calcd. | 48.69 | 7.21 | 10.02 |
| Found | 49.08 | 7.04 | 10.06 |

EXAMPLE 19

In 140 ml of ethyl acetate were dissolved 11.84 g of the 4-dimethylamino-2-(3,4,5-trimethoxyphenyl)butyramide obtained in Example 1 and 9.75 g of (−)-cis-2-benzamidocyclohexanecarboxylic acid with heating, and the mixture was allowed to stand for 14 hours. The mixture was then filtered to give a crystalline fraction and a mother liquor fraction. The crystals collected by filtration were dried under reduced pressure. These crystals (11.44 g) were recrystallized from 120 ml of acetone to provide 7.89 g of crystals. These crystals were further recrystallized from 100 ml of acetone to give 6.03 g of crystals ($[\alpha]_D^{20} = -49.0$ (c=1.0, MeOH)). The crystals were suspended in 150 ml of ethyl acetate and washed with 10% aqueous solution of sodium carbonate twice and saturated aqueous solution of sodium chloride three times to provide a clear ethyl acetate solution. This ethyl acetate solution was dried over anhydrous sodium sulfate and concentrated to dryness under reduced pressure to provide 2.23 g of solid. To a solution of this solid residue in 15 ml of ethanol was added 0.75 ml of concentrated hydrochloric acid. The mixture was allowed to stand at 4° C. overnight and the resulting crystals were collected by aspiration and dried under reduced pressure to provide 1.96 g of (−)-4-dimethylamino-2-(3,4,5-trimethoxyphenyl)butyramide hydrochloride.

$[\alpha]_D^{20} = -60.7$ (c=1.0, MeOH)

Elemental analysis for $C_{15}H_{25}N_2O_4Cl \cdot 0.6\ H_2O$

|  | C (%) | H (%) | N (%) | Cl (%) |
|---|---|---|---|---|
| Calcd. | 52.43 | 7.68 | 8.15 | 10.32 |
| Found | 52.47 | 7.69 | 8.18 | 10.26 |

Melting point: 201°–203° C.

The mother liquor fraction separated as above was washed with 15% aqueous solution of sodium carbonate twice and saturated aqueous solution of sodium chloride 3 times, dried over anhydrous sodium sulfate and then concentrated to dryness to give 3.49 g of solid. This solid and 2.33 g of (+)-cis-2-benzamidocyclohexanecarboxylic acid were dissolved in 80 ml of ethyl acetate with heating and the solution was allowed to stand for 4 hours. The resulting crystals were collected by aspiration and dried. The resulting crystals (4.72 g) were recrystallized from 50 ml of acetone to provide 3.33 g of crystals. $[\alpha]_D^{20} = +49.8$ (c =1.0, MeOH). These crystals were suspended in 100 ml of ethyl acetate and washed with 10% aqueous solution of sodium carbonate twice and saturated aqueous solution of sodium chloride three times to provide a clear ethyl acetate solution. This ethyl acetate solution was dried over anhydrous sodium sulfate and concentrated to dryness under reduced pressure to give 1.37 g of solid. To a solution of this solid in 9.5 ml of ethanol was added 0.46 of concentrated hydrochloric acid. The mixture was allowed to stand at 4° C. overnight and the resulting crystals were collected by aspiration and dried under reduced pressure to provide 1.18 g of (+)-4-dimethylamino-2-(3,4,5-trimethoxyphenyl)butyramide hydrochloride.

$[D]_D^{20} = +59.9$ (c=1.0, MeOH)

Elemental analysis for $C_{15}H_{25}N_2O_4Cl \cdot 0.5\ H_2O$

|  | C (%) | H (%) | N (%) | Cl (%) |
|---|---|---|---|---|
| Calcd. | 52.71 | 7.67 | 8.20 | 10.37 |
| Found | 52.60 | 7.62 | 8.17 | 10.43 |

Melting point: 201°–202° C.

The two optically active compounds obtained above both showed an optical purity of 99.9% when analyzed by high performance liquid chromatography using an optically active column.

Column: $\alpha_1$-AGP (4.0 mm i.d.×10 cm)
Column temperature: 25° C.
Eluent: 0.03M phosphate buffer pH 6.5
Flow rate: 0.8 ml/min.
Detection: UV230 nm Examples of the preparation containing the compound of the present invention are described below.

FORMULATION EXAMPLE 1
(Inhalant)
Powdery inhalant

| Compound of Example 14 | 1 mg |
|---|---|
| Lactose | 39 mg |
|  | 40 mg |

1 g of the compound of Example 14 and 39 g of lactose are evenly blended, pulverized, sieved, and filled into No. 3 capsule shells by using a capsule machine to provide a powdery inhalant.

FORMULATION EXAMPLE 2
(Inhalant)
Suspension

| Compound of Example 14 | 0.15 g |
|---|---|
| Sorbitan trioleate | 0.21 g |
| Dichloromonofluoromethane | 5.16 g |
| Dichlorotetrafluoroethane | 5.16 g |
| Dichlorodifluoromethane | 10.32 g |
|  | 21.0 g |

150 g of the compound of Example 14 and 210 g of sorbitan trioleate are evenly blended. A 0.36 g portion of the resulting mixture is filled into a 20 ml aluminum can, which is then clinched following insertion of a valve device. Then, using a compressed gas biuret, the propellant in a predetermined amount is sealed into the can under pressure to provide an aerosol product.

FORMULATION EXAMPLE 3
(Inhalant)
Solution

| Compound of Example 14 | 0.15 g |
|---|---|
| Distilled water | 4.2 ml |
| Benzalkonium chloride | 0.01 g |
| Dichloromonofluoromethane | 5.16 g |
| Dichlorotetrafluoroethane | 5.16 g |
| Dichlorodifluoromethane | 10.32 g |
|  | 25.0 g |

150 g of the compound of Example 14, 10 g of benzalkonium chloride and 4.2 l of distilled water are evenly blended. A 4.36 g portion of the resulting mixture is filled into a 20 ml aluminum can, which is then clinched following insertion of a valve means. Then, using a compressed gas biuret, the propellant in a predetermined amount is sealed into the can under pressure to provide an aerosol product.

FORMULATION EXAMPLE 4
Tablet

| | |
|---|---|
| Compound of Example 14 | 100 mg |
| Lactose | 56 mg |
| Corn starch | 37 mg |
| Hydroxypropylcellulose | 6 mg |
| Magnesium stearate | 1 mg |
| Total | 200 mg |

100 g of the compound of Example 14, 56 g of lactose and 37 g of corn starch are evenly blended. Then, 60 g of 10% hydroxypropylcellulose solution is added thereto and the mixture is wet-granulated. After sieving, the granules are dried. To the granules is added 1 g of magnesium stearate, following by mixing. Using an 8 m/m 6.4R punch, the granules are compression-molded to provide tablets.

FORMULATION EXAMPLE 5
Capsule

| | |
|---|---|
| Compound of Example 14 | 50 mg |
| Crystalline cellulose | 40 mg |
| Crystalline lactose | 109 mg |
| Magnesium stearate | 1 mg |
| Total | 200 mg |

50 g of the compound of Example 14, 40 g of crystalline cellulose, 109 g of crystalline lactose and 1 g of magnesium stearate are evenly blended, and the mixture is filled into No. 3 capsule shells by using a capsule filling machine to provide capsules.

FORMULATION EXAMPLE 6
Lyophylizate per vial:

| | |
|---|---|
| Compound of Example 14 | 25 mg |
| D-mannitol | 33 mg |
| Total | 58 mg |

In 800 ml of water are dissolved 25 g of the compound of Example 14 and 33 g of D-mannitol in that order and the solution is made up to 1 l with water. This solution is aseptically filtered, filled in 1 ml portions into vials and freeze-dried to provide an injection for extemporaneous reconstitution.

What is claimed is:

1. A tri(lower alkoxy)benzene derivative represented by the general formula (I), or a salt, optical isomer or solvate thereof:

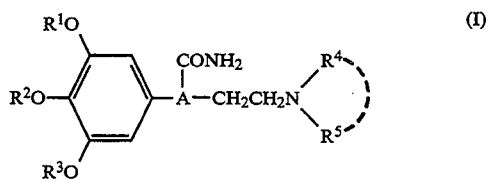

wherein $R^1$, $R^2$ and $R^3$, which are the same or different, each represents a lower alkyl group; A represents a group of the formula

and $R^4$ and $R^5$, which are the same or different, each represents a lower alkyl group, an aralkyl group or an aryl group.

2. The compound as claimed in claim 1, wherein $R^4$ and $R^5$, which are the same or different, each represents a lower alkyl group.

3. The compound as claimed in claim 1 or 2, wherein both of $R^4$ and $R^5$ represent a methyl group.

4. The compound as claimed in any of claims 1 to 3 which is a salt and/or an optically active compound.

5. 1-(2-Dimethylaminoethyl)-1-(3,4,5-trimethoxyphenyl)urea or its hydrochloride.

6. 4-Dimethylamino-2-(3,4,5-trimethoxyphenyl)-butyramide or a salt thereof, or an optically active form of either compound.

7. A pharmaceutical composition comprising said tri(lower alkoxy)benzene derivative (I), salt, optical isomer or solvate of claim 1 and a pharmaceutically acceptable carrier.

8. The pharmaceutical composition of claim 7, which is suitable for treating and preventing respiratory ailment.

9. A method of treating and preventing respiratory ailment in a patient which comprises administering a therapeutically effective amount of the pharmaceutical composition as described in claim 7 to the patient.

* * * * *